United States Patent [19]

Jacobs

[11] 4,262,541

[45] Apr. 21, 1981

[54] METHOD OF AGE TESTING RUBBER BASED PROPELLANTS

[75] Inventor: Merrit Jacobs, Waldorf, Md.

[73] Assignee: The United States of America as represented by the Secretary of the Navy, Washington, D.C.

[21] Appl. No.: 24,645

[22] Filed: Mar. 28, 1979

[51] Int. Cl.³ .............................................. G01N 3/08
[52] U.S. Cl. .......................................... 73/826; 73/824
[58] Field of Search ................. 73/15.6, 826, 834, 159

[56] References Cited

U.S. PATENT DOCUMENTS

| 2,709,359 | 5/1955 | Koch et al. | 73/15.6 |
| 2,768,068 | 10/1956 | Juve et al. | 73/15.6 |
| 3,582,282 | 6/1971 | Kampf et al. | |
| 3,868,221 | 2/1975 | Howard et al. | 73/159 |

OTHER PUBLICATIONS

Newton, "Mechanism of Exposure-Cracking of Rubber", in Journal of Rubber Research, vol. 14, 4/45, pp. 41-59.

Chemical Abstracts, vol. 841645LT, vol. 85125424C, vol. 85144408S, all 1976.

Primary Examiner—Herbert Goldstein
Attorney, Agent, or Firm—R. S. Sciascia; A. L. Branning

[57] ABSTRACT

A method of testing the aging properties of a rubber-based propellant by exposing a stressed sample of the rubber-based propellant to a controlled flow of air containing a carefully controlled concentration of ozone, and periodically measuring the physical properties.

2 Claims, 7 Drawing Figures

FIG. 1

MECHANICAL PROPERTY DATA FOR PROPELLANT A (CTPB)

FIG. 2

MECHANICAL PROPERTY DATA FOR PROPELLANT B (HTPB)

FIG. 3

○ ORIGINAL  ■ DESICCATOR
● LAB CONTROL  □ OZONE
C = CRACK

MECHANICAL PROPERTY DATA FOR PROPELLANT C (CTPB)

FIG. 4

○ ORIGINAL   ■ DESICCATOR CONTROL
● LAB CONTROL   □ OZONE
B = BREAK   C = CRACK

MECHANICAL PROPERTY DATA FOR PROPELLANT D (HTPB)

*FIG. 5*

○ ORIGINAL ■ DESICCATOR CONTROL
● LAB CONTROL □ OZONE
B = BREAK C = CRACK

MECHANICAL PROPERTY DATA FOR PROPELLANT E (CTBN)

FIG. 6

○ ORIGINAL   ■ DESICCATOR CONTROL   D¹ = DATA RANGE DESCISSATOR CONTROL
● LAB CONTROL   □ OZONE   D² = DATA RANGE OZONE

MECHANICAL PROPERTY DATA FOR PROPELLANT F (URETHANE)

*FIG. 7*

METHOD OF AGE TESTING RUBBER BASED PROPELLANTS

BACKGROUND OF THE INVENTION

This invention relates to propellants and more particularly to rubber-based propellants.

Rubber-based propellants must be flexible and strong enough to withstand tremendous pressures and shocks which occur when the propellant is ignited. Otherwise, the propellant will crack and break and thus burn improperly. Unfortunately, rubber-based propellants become less flexible and less strong as they age. It is important, therefore, to find rubber-based propellant composite which resist the aging process.

An important aspect of the search is the testing of the aging properties of various rubber-based propellant composites. Simply exposing the propellants to normal environmental conditions is impractical because of the length of time such testing takes. One prior art approach is to expose the propellants to high temperatures (e.g. 140° F.–165° F.). The data from such test provide only a vague indication of the aging properties of the tested propellants. This is due in part to reactions between propellant ingredients which occur at elevated temperatures but do not occur at ambient storage temperatures.

The influence of ozone on the rate of cracking of strained rubber samples has been studied (see, for example, Newton, R.G.; "Mechanism of Exposure-Cracking of Rubbers," Journal of Rubber Research, volume 14, No. 4 (April 1945), pp 39–63.) These prior art tests focus on the study and characterization of cracks which appear in the rubber sample. This data is of little value in evaluating the useful life of rubber-based propellants. Well before cracks appear the rubber-based propellants usually have lost the minimum strength and flexibility which they need for proper ignition and burning.

SUMMARY OF THE INVENTION

Accordingly, one object of this invention is to provide a practical method of determing or predicting the useful life of rubber-based propellants composites.

Another object of this invention is to provide a method of accurately determining or predicting the useful life of rubber-based propellant composites.

A further object of this invention is to provide a method of testing the aging properties of rubber-based propellant compositions which will provide reproducible results.

Yet another object of this invention is to provide a method of comparing the aging properties of different rubber-based composites. These and other objects of this invention are achieved by providing a method of testing (1) exposing a stressed sample of the rubber-based propellant to a controlled flow of air containing a carefully controlled concentration of ozone; and (2) periodically measuring the physical properties of the rubber-based propellant.

BRIEF DESCRIPTION OF THE DRAWINGS

A more complete appreciation of the invention and many of the attendant advantages thereof will be readily appreciated as the same becomes better understood by reference to the following detailed description when considered in connection with the accompanying drawings wherein.

DETAILED DESCRIPTION OF THE PREFERRED EMBODIMENT

Figure 1:
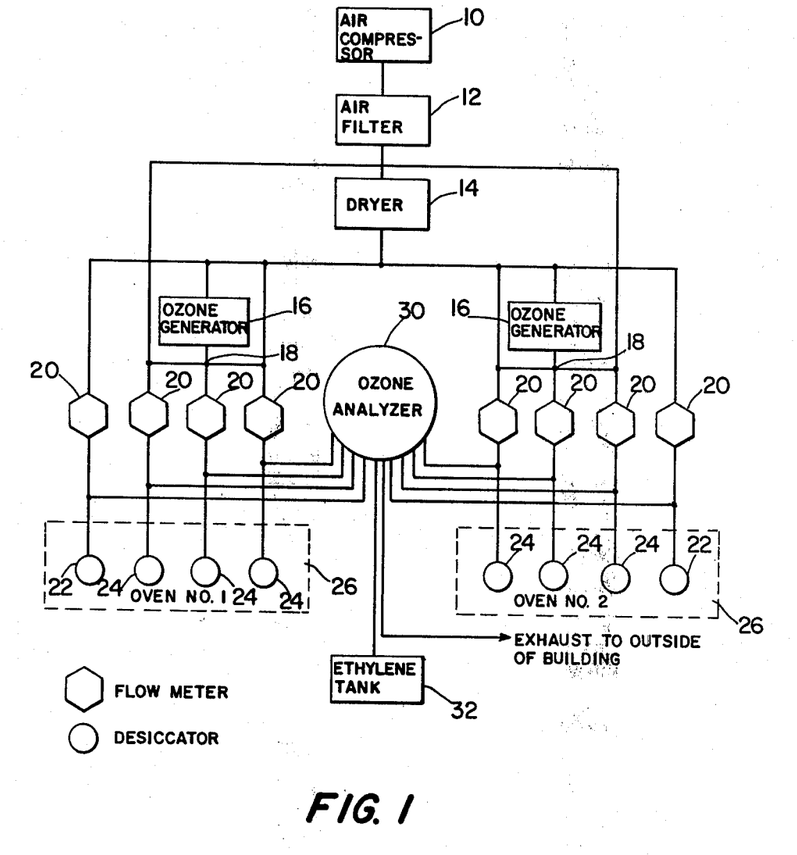
FIG. 1 is a block diagram of the ozone propellant aging apparatus.
Figure 2:
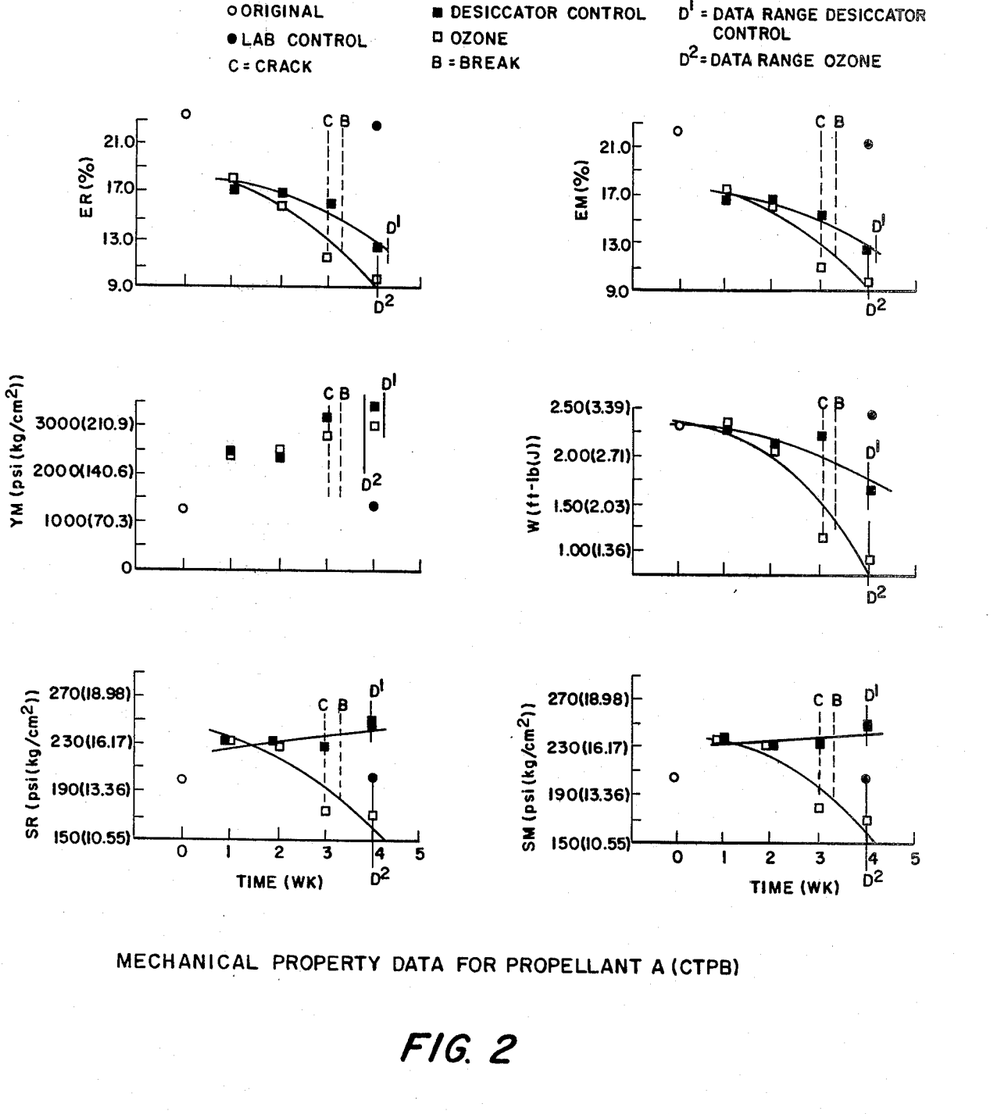
FIGS. 2 through 7 consist of graphs showing physical property data obtained by testing various rubber-based propellant composites with the method of the present invention.
Figure 3:
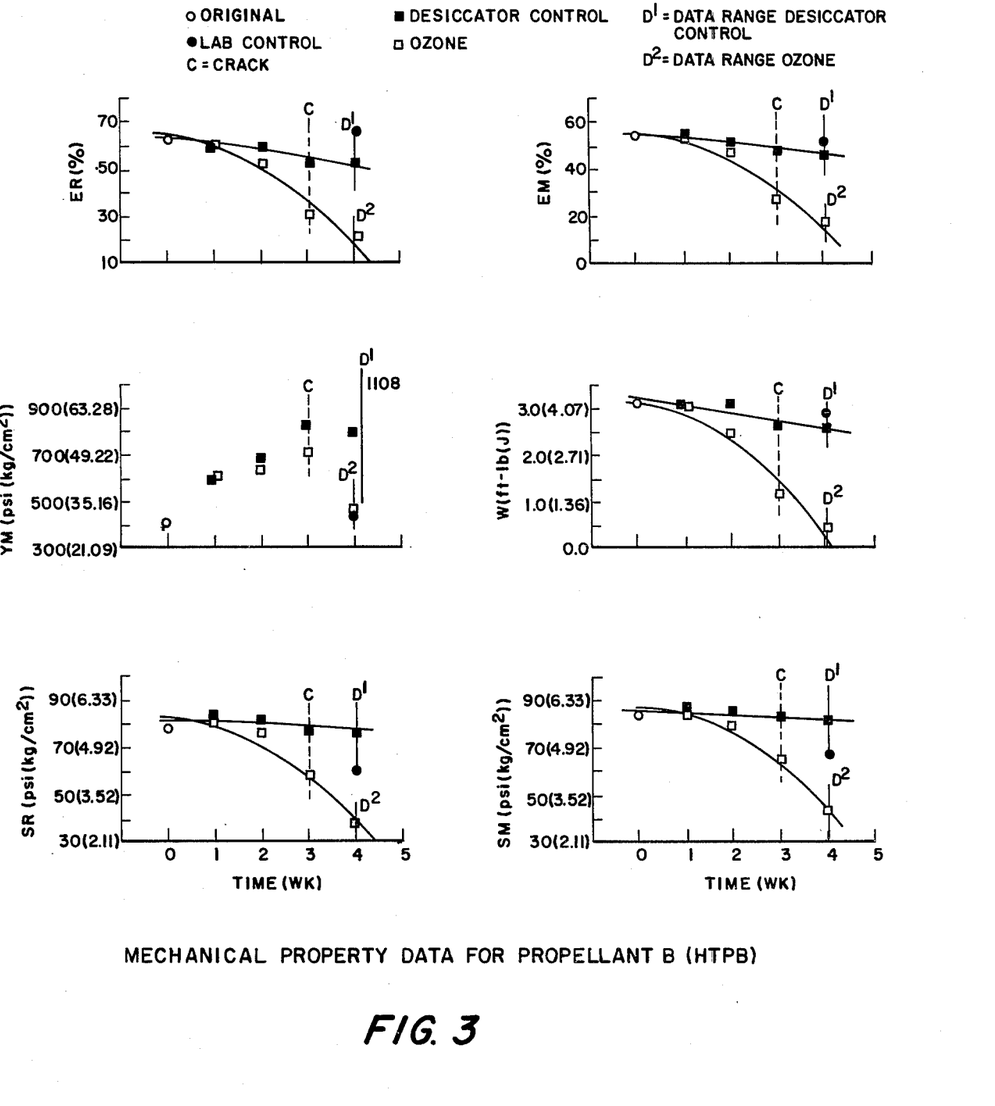

A typical example of ozone accelerated aging equipment to be used in the method of the present invention is shown in FIG. 1. An air compressor 10 supplies a regulated amount of air which then passes through an air filter 12. The humidity of the air can be adjusted by directing some of the air flow through a dryer 14 and allowing the remainder of the air to by-pass the dryer. The air is then passed through an ozone generator 16, a distribution manifold 18, and flow meters 20, and into sample desiccators 24 which hold the samples. A control sample may be placed into a control desiccator 22 into which dry, unozonized air is passed.

Ultraviolet (UV) radiation is used to convert oxygen in the air to ozone in the generators 16 and the level of ozone is controlled by the amount of exposure of the ultraviolet source to the air flow. The ozone level is carefully monitored and an ozone analyzer 30 (such as the Bendix Model 8002). The Bendix Model 8002 ozone analyzer 30 uses a photometrix method detecting the chemiluminescence reaction of ozone and ethylene which is supplied from a tank 32. The analyzer 30 is connected so as to measure both input and exhaust ozone levels of any of the sample desiccators 24 or control desiccators 22.

An ozone level of from 10 to 1000 parts of ozone for every billion parts of air (PPB) is preferred, with from 200 to 800 PPB being more preferred. For a valid comparison of the physical properties of different rubber-based propellant composites, it is critical that the samples are exposed to the same concentrations of ozone. Therefore, it is important that the ozone concentration is carefully monitored and controlled.

The desiccators 22 and 24 used were standard 7.4-quart (7-liter) glass chambers housed in temperature controlled ovens 26. The ozone/air mixture is introduced at the bottom of the desiccators since the mixture has a high specific gravity than air. The mixture then exits through the top of the desiccator 20.

The oven temperature is preferably in the range of from about 30° C. to about 50° C. Higher temperatures may cause the propellant ingredients to react with each other and produce invalid results.

During the exposure to the ozone the propellant sample is strained.

Periodically, the following physical properties relating to the strength and flexibility of the propellant are determined: maximum tensile (SM), tensile at rupture (SR), percent elongation at maximum tensile (EM), percent elongation at rupture (ER), young's modulus (YM), and work input (W). Measurement of other physical properties may also be made. Additionally, the samples should be watched for cracks or breaks during the testing.

EXPERIMENTAL

Six propellant formulations were tested; five were formulated with butadiene binders and one containing a polypropylene glycol/toluene diisocyanate urethane binder. The butadiene propellants included one of the following: hydroxyl-terminated polybutadiene (HTPB), carboxyl-terminated polybutadiene (CTPB), or carboxyl-terminated polybutadiene acrylonitrile (CTBN).

For each of the tested propellants, standard JANNAF die-cut dogbones of 0.25 in. (0.635-cm) thickness were prepared except for propellant A where 0.50-in. (1.27-cm) thick samples were used. These propellants were then subjected to tensile testing using Instron Machines Model TM and TTC. These tests were conducted at a strain rate of 0.7407 in/in/min (0.7407 cm/cm/min) at 77° F. (20.5° C.) for all but propellant F which was tested at the same strain level but a temperature of 0° F. (−10.8°). The strain rate and temperature conditions selected correspond to the respective propellant's acceptance procedures. The following mechanical properties were determined for each of the propellants tested: maximum tensile (SM), tensile at rupture (SR), percent elongation at maximum tensile (EM), percent elongation at rupture (ER), Young's modulus (YM), and work input (W).

Following these tests the remaining dogbone samples were divided into three groups. Group I, a laboratory control sample, was wrapped in aluminum foil and held at room temperature. Groups II and III were strained to 6.5% of their initial gauge length and were placed into the aluminum/glass straining fixture. The straining fixtures and propellant were then placed into desiccators held at 122° F. (50° C.). In one set of desiccators a 300 parts per billion (ppb) ozone concentration was introduced as a regulated component of the airflow. The second set was used as a control set (desiccator control) and had an ozone level of 0 to 1 ppb. The air or air/ozone flow rate through both sets of desiccators was 0.0706 ft$^3$/min (2 liters/min).

Visual checks were made daily for propellant cracking, breakage, or any other visually detectable occurrence. At this time, measurements of the ozone levels (both into and from the desiccators), flow rates, and the conditioning temperature were made.

At weekly intervals, the propellant and straining fixtures were removed from the desiccators. The input stress on the propellant sample was removed thereby allowing the propellant to relax. After a 2-hour relaxation period, and relaxed gauge length of the dog-bone explosed to the 300 ppb ozone level was remeasured, and these samples together with the desiccator control samples were subjected to the mechanical property testing as detailed earlier. The remaining samples were restrained to 6.5% of their new or post-relaxation gauge length and were returned to the desiccators. The desiccator control (0 to 1 ppb ozone level) samples were restrained to the length computed by the measurement of the ozone exposed samples. Unlike the ozone and the desiccator control samples, the laboratory control samples were subjected to mechanical property testing only at the conculsion of the 4- week test period.

Figure 4:
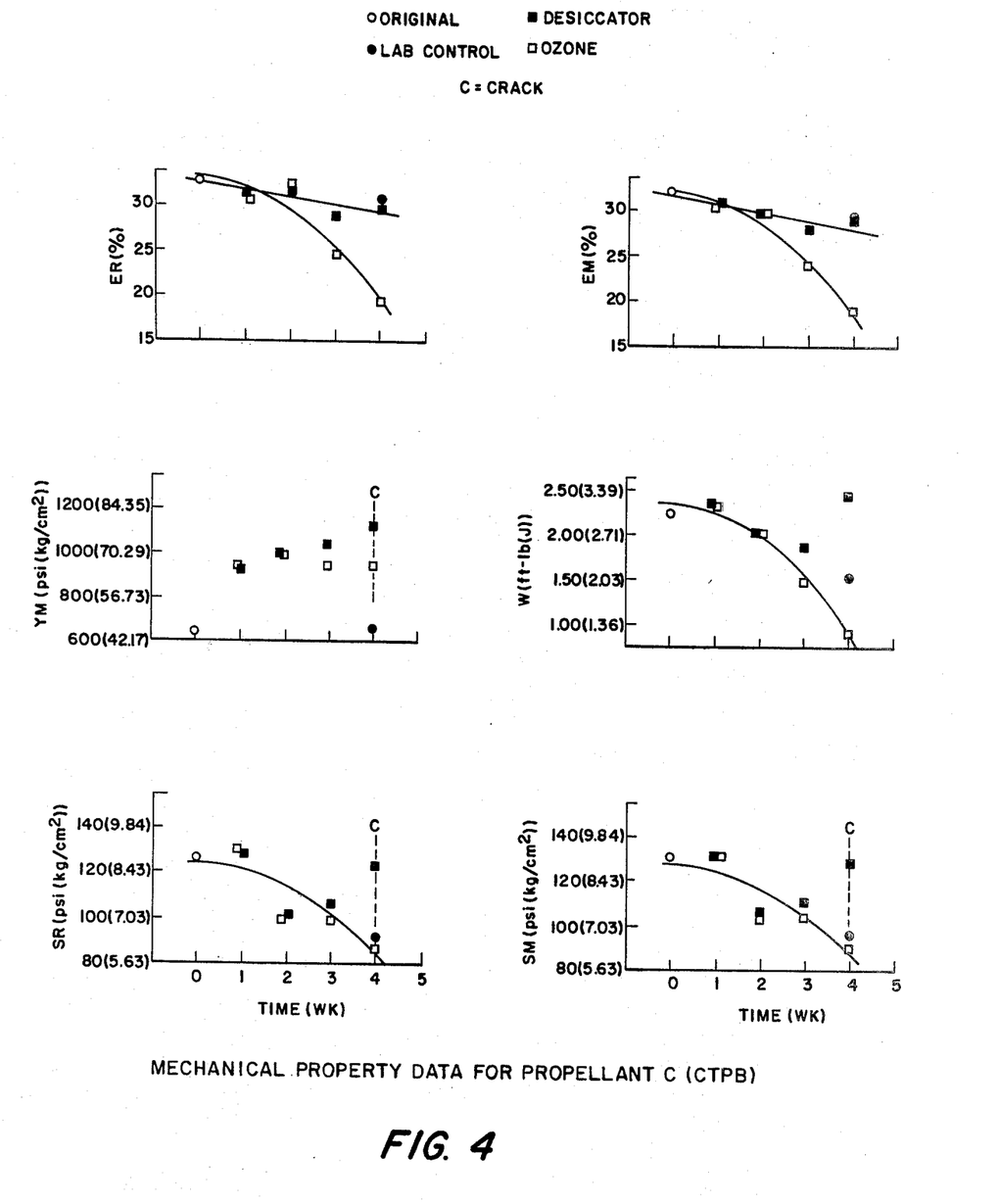
Figure 5:
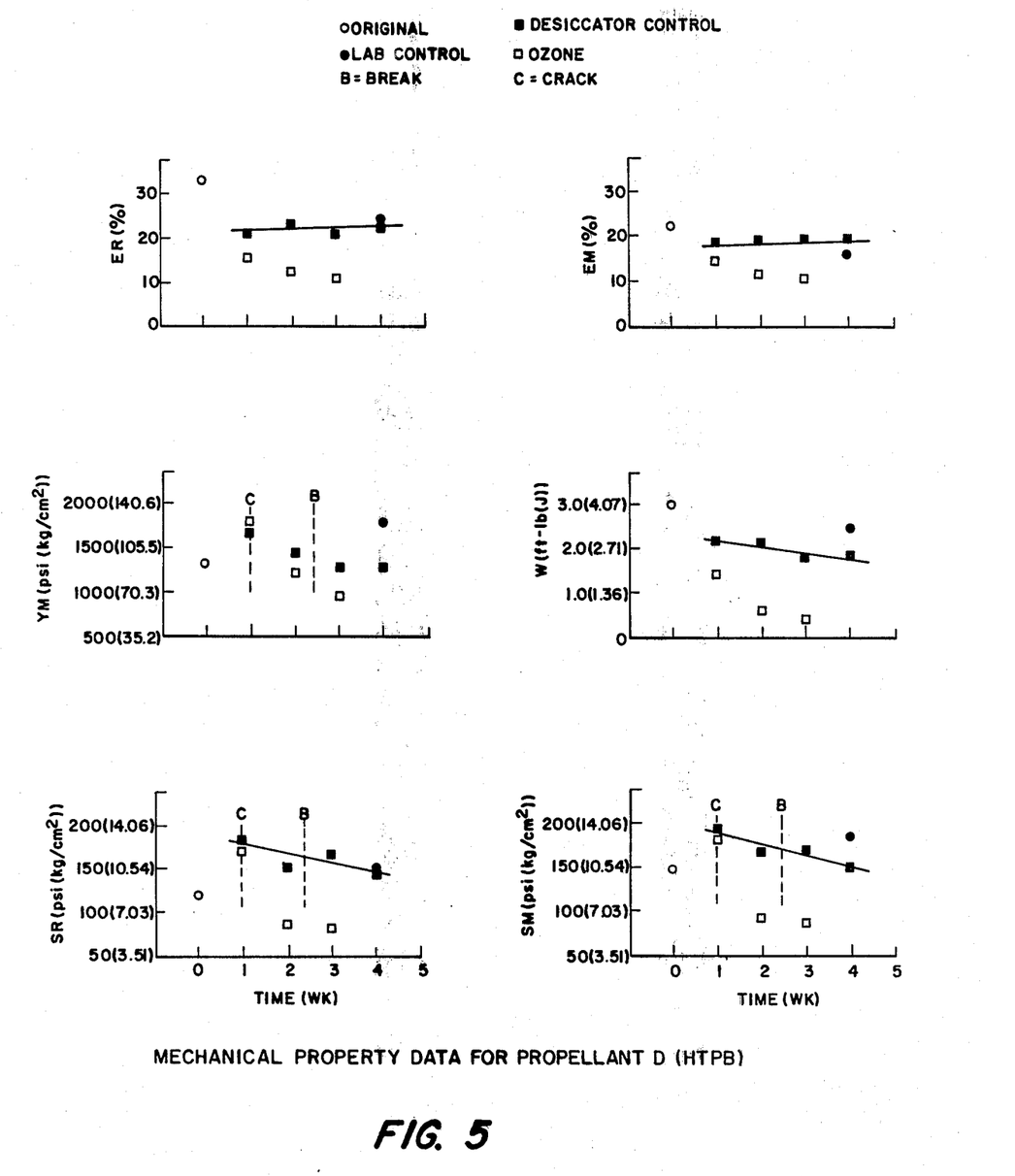
Figure 6:
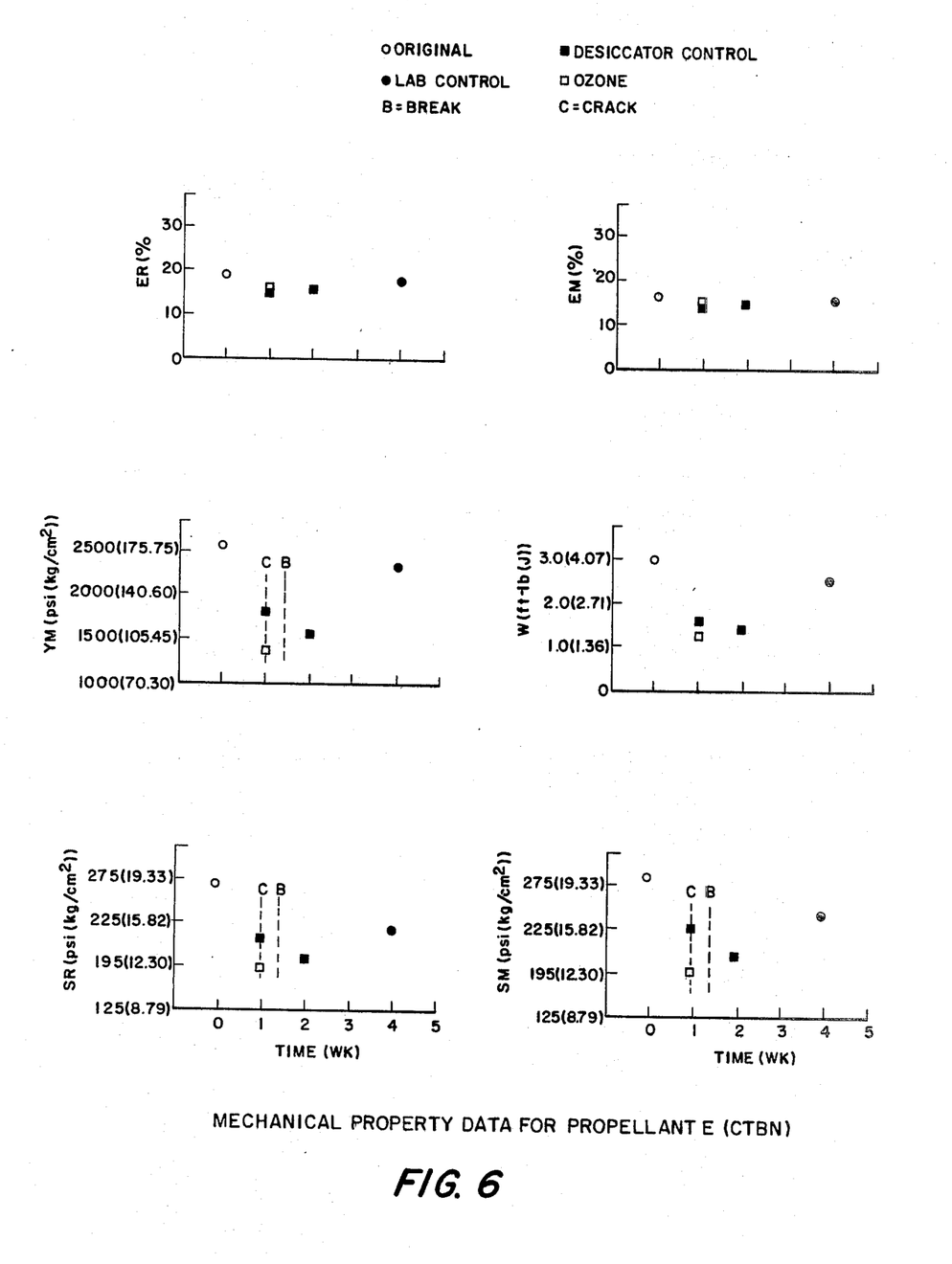
Figure 7:
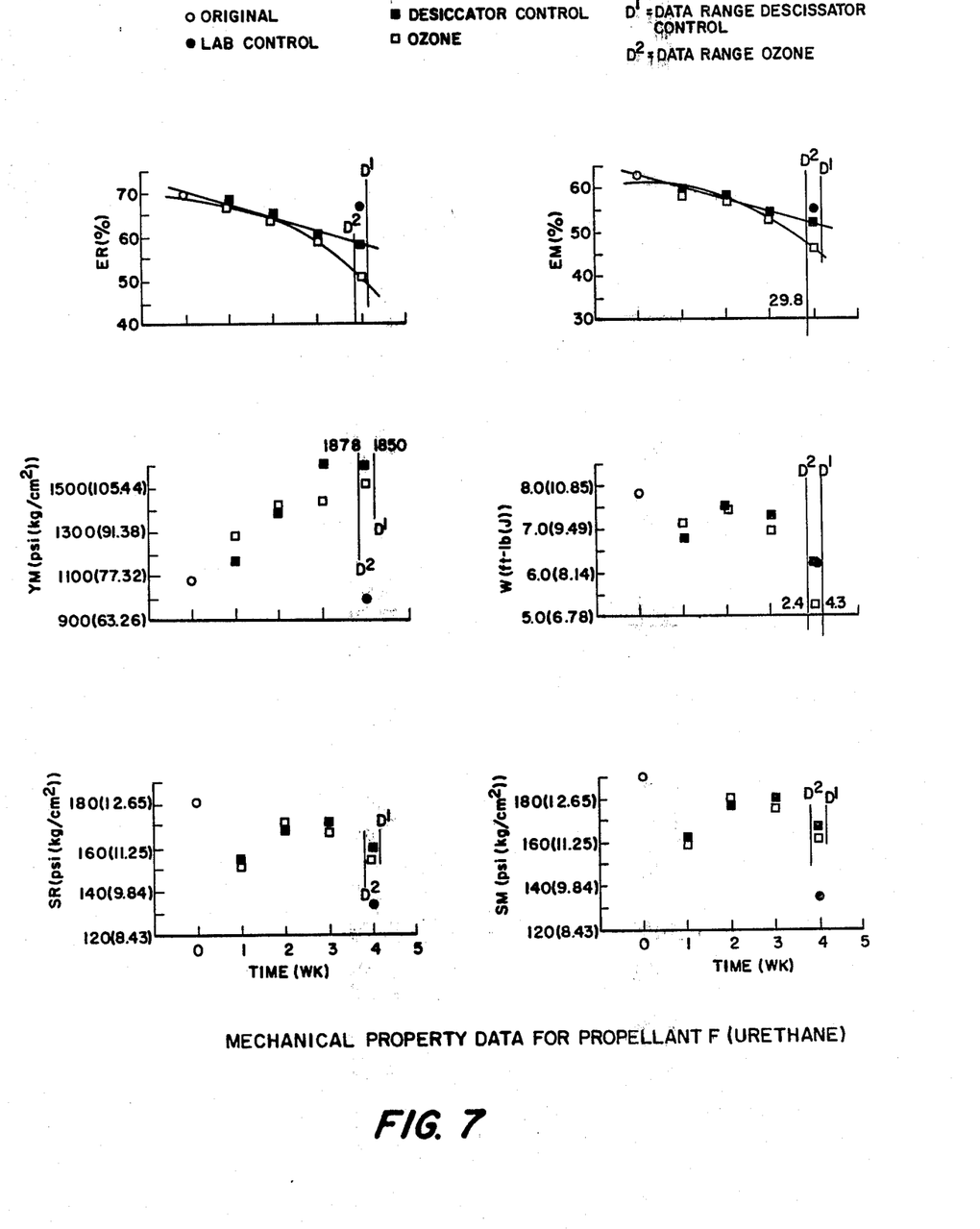

All propellants formulated with a polybutodiene binder showed statistically significant differences in mechanical properties between the desiccator control and the ozone exposed samples. Over the 4-week testing period propellants exposed to ozone showed evidence of cracking, and three of the five experienced broken dogbones. Except for an increase in Young's modulus, mechanical property values for all parameters decreased with exposure time to ozone. These general trends are shown in FIG. 4 for propellant A (a CTPB binder lead nitrate oxidizer formulation) and in FIG. 5 for propellant B (an HTPB binder propellant with an ammonium perchlorate oxidizer). Both propellants showed significant differences between the desiccator control and ozone exposed samples. In spite of these differences the control samples maintained higher values for all parameters. These results held true for all the propellants tested as shown in FIGS. 6 through 9 for propellants C through F.

The time to first cracking and breakage of the propellant JANNAF dogbones exposed to ozone was noted for all the propellants tested. These data are presented in Table I. Although this information is not as quantitative as mechanical properties, it does indicate the point at which considerable degradation has occurred.

TABLE I

CRACKING AND BREAKAGE DATA

| Propellant | Time to crack (wk) | Time to break (wk) |
| --- | --- | --- |
| A (CTBP/lead nitrate | 3 | 3¼ |
| B (HTPB/ammonium perchlorate) | 3 | — |
| C (CTPB/ammonium perchlorate) | 4 | — |
| D (HTPB/ammonium perchlorate) | 1 | 2¼ |
| E (CTBN/ammonium perchlorate) | 1 | 1¼ |
| F (urethane/ammonium perchlorate) | — | — |

Although ozone exposed samples always showed the greatest change in mechanical properties, major differences in test data were also noted between desiccator control samples and both zero-time propellant and laboratory control samples. Numerically, similar changes are measured for samples stored under ozone for the duration of 1 week and most probably were not caused by oxidation. A likely reason for this shift in mechanical property test data is the loss of volatiles caused by the airflow through the desiccators. Another possible contributing factor is a postcure triggered by the elevated temperatures seen by the desiccator samples.

Propellants C and F show major differences in mechanical properties between the original and the 4-week laboratory control data. It is theorized that the reason for this effect was that these two propellants are more susceptible to moisture than the other types tested.

The post relaxation gauge length measurements give an indictation of the propellant's susceptibility to creep with increasing ozone exposure time. The data in Table II indicate that most of the propellants continue to creep during the 4 weeks of testing although the percent change in relaxed length decreased with time. The same data in Table II are presented in FIG. 11. A comparison of all propellants illustrates that differences in the tendency to creep can be related to the ratio of the imposed percent strain level (6.5%) to maximum percent elongation. A reduction in creep with time is consistent with the expected hardening effect from an oxidation reaction.

Obviously numerous modifications, and variations of the present invention are possible in light of the above teachings. It is therefore to be understood that, within the scope of the appended claims, this invention may be practiced otherwise than as specifically described.

What is claimed as new and desired to be secured by Letters Patent of the United States is:

TABLE II

RELAXED LENGTH DATA

| Time on Test (wk) | Relaxed length [cm(in.)] | Change from previous length [cm(in.)] | % Change | Time on test (wk) | Relaxed length [cm(in.)] | Change from previous length [cm(in.)] | % Change |
|---|---|---|---|---|---|---|---|
| Propellant A (CTPB) | | | | Propellant D (HTPB) | | | |
| 0 | 5.29(2.08) | — | — | 0 | 5.32(2.09) | — | — |
| 1 | 5.50(2.16) | 0.21(0.08) | 4.0 | 1 | 5.60(2.20) | 0.28(0.11) | 5.3 |
| 2 | 5.72(2.26) | 0.23(0.08) | 4.2 | 2 | 5.70(2.24) | 0.10(0.04) | 1.8 |
| 3 | 5.92(2.33) | 0.20(0.07) | 3.5 | 3 | 5.70(2.24) | 0.00 | 0.0 |
| Propellant B (HTPB) | | | | Propellant E (CTBN) | | | |
| 0 | 5.31(2.09) | — | — | 0 | 5.25(2.07) | — | — |
| 1 | 5.54(2.18) | 0.23(0.09) | 4.3 | 1 | 5.47(2.15) | 0.22(0.08) | 4.2 |
| 2 | 5.72(2.25) | 0.18(0.07) | 3.2 | | | | |
| 3 | 5.75(2.26) | 0.03(0.01) | 0.5 | | | | |
| Propellant C (CTPB) | | | | Propellant F (Urethane) | | | |
| 0 | 5.30(2.09) | — | — | 0 | 5.27(2.07) | — | — |
| 1 | 5.40(2.12) | 0.10(0.03) | 1.9 | 1 | 5.53(2.17) | 0.26(0.10) | 4.9 |
| 2 | 5.56(2.19) | 0.16(0.07) | 3.0 | 2 | 5.67(2.23) | 0.14(0.06) | 2.5 |
| 3 | 5.65(2.22) | 0.09(0.03) | 1.6 | 3 | 5.76(2.26) | 0.09(0.03) | 1.6 |

1. A method of testing the aging properties of a rubber-based propellant comprising the steps of:
   (1) exposing a plurality of stressed samples of the rubber-based propellant to a controlled flow of air containing from 10 to 1,000 parts of ozone per billion parts of air and a carefully controlled concentration of moisture; and
   (2) periodically determining the maximum tensile, the tensile at rupture, the percent elongation at maximum tensile and at rupture of the rubber-based-propellant samples.

2. The method of claim 1 wherein the ozone concentration is from 200 to 800 parts billion parts of air.

* * * * *